(12) United States Patent
Fishman

(10) Patent No.: US 7,291,591 B2
(45) Date of Patent: *Nov. 6, 2007

(54) ALCOHOL-FREE TRANSDERMAL INSULIN COMPOSITION

(75) Inventor: Robert Fishman, Pembroke Plnes, FL (US)

(73) Assignee: All Natural FMG, Inc., North Palm Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/407,387

(22) Filed: Apr. 18, 2006

(65) Prior Publication Data

US 2006/0280782 A1    Dec. 14, 2006

Related U.S. Application Data

(63) Continuation-in-part of application No. 10/412,637, filed on Apr. 11, 2003, now Pat. No. 7,033,998.

(51) Int. Cl.
*A61K 9/70* (2006.01)
*A61K 38/28* (2006.01)

(52) U.S. Cl. .............................. 514/3; 514/4; 424/449; 530/303

(58) Field of Classification Search .................... None
See application file for complete search history.

(56) References Cited

U.S. PATENT DOCUMENTS 6,958,154 B2 * 10/2005 Andolino Brandt et al. ..... 424/400
7,033,998 B2 * 4/2006 Fishman ....................... 514/3

* cited by examiner

*Primary Examiner*—Anish Gupta
*Assistant Examiner*—Julie Ha
(74) *Attorney, Agent, or Firm*—McHale & Slavin, P.A.

(57) ABSTRACT

The instant invention is directed toward a dermal delivery system composition comprising an aqueous base vehicle including Emu oil, at least one fatty acid alkyl ester, polyethylene glycol, and a gelling agent, in combination with a therapeutically effective amount of at least one species of insulin, and to processes for the manufacture and use thereof.

6 Claims, No Drawings

ALCOHOL-FREE TRANSDERMAL INSULIN COMPOSITION

CROSS REFERENCE TO RELATED APPLICATION

This application is a continuation-in-part of U.S. patent application Ser. No. 10/412,637, filed Apr. 11, 2003 now U.S. Pat. No. 7,033,998, the contents of which are herein incorporated by reference.

FIELD OF THE INVENTION

This invention relates to an insulin composition in combination with an alcohol-free dermal delivery system for transdermal application and to processes for manufacture and use thereof.

BACKGROUND OF THE INVENTION

Insulin is a naturally occurring hormone secreted by the beta cells of the islands of Langerhans in the pancreas in response to increased levels of glucose in the blood. The hormone acts to regulate the metabolism of glucose and the processes associated with the intermediary metabolism of fat, carbohydrates and proteins. Insulin lowers blood glucose levels and promotes transport and entry of glucose into muscle cells and other tissues. Due to the chemical nature of insulin molecules, the traditional route of insulin administration in diabetic patients, who require multiple daily doses of insulin, is intradermal or subdermal injection.

Prior art efforts to develop a non-injectable transdermal insulin delivery system for the treatment of diabetes have not been successful to date. While insulin can be systemically delivered to a patient by the topical application of an insulin-containing vehicle, the systemic blood levels of insulin that are achievable using this delivery method have proven to be generally inadequate for meeting the demands of the diabetic patient.

Various methods have been developed for enhancing the transdermal delivery of insulin including improved passive diffusion carriers for increasing the permeability of the epidermis, sonophoresis, iontophoresis and ionosonic transport. Passive diffusion through the outer layer of skin has been used successfully for the delivery of low molecular weight lipophilic drugs such as scopolamine, estradiol and nitroglycerine, but has been largely unsuccessful for the transdermal delivery of hydrophilic peptides such as insulin due to the low skin permeability of such peptides. Thus, mechanical vibrational energy and/or iontophoresis are employed to increase skin permeability and facilitate transdermal insulin delivery. Sibalis et al., in U.S. Pat. No. 4,940,456, teaches an apparatus and method for the iontophoretically mediated transdermal delivery of insulin. Henley, in U.S. Pat. Nos. 5,667,487 and 5,658,247 discloses an ionosonic apparatus suitable for the ultrasonic-iontophoretically mediated transport of therapeutic agents across the skin. Insulin has a tendency to form dimers and hexamers in pharmacological compositions, which are considered to be too large for transdermal delivery. Brange, in U.S. Pat. No. 5,597,796, suggests chemically modifying insulin to produce insulin analogs that resist intermolecular association and enable improved iontophoretic delivery. Jang et al., in U.S. Pat. No. 5,681,580, discloses a patch containing insulin formulated in a gel for the iontophoretically driven transdermal delivery of insulin. Notwithstanding the advances in methods for the transdermal delivery of insulin described above, the transdermal delivery of insulin in a quantity sufficient to attain a therapeutic level in the blood of diabetic patients has heretofore not been possible.

Clinical use of transdermal drug delivery has been limited because very few drugs are able, at least by passive diffusion alone, to penetrate the skin at a sufficient rate to produce a useful systemic drug concentration in the patient. The outer layer of the skin, the stratum corneum, is a major barrier to diffusion of low and especially high molecular weight drugs across the skin to the bloodstream. One drug for which an effective transdermal delivery system has long been sought is insulin, a therapeutic agent useful in the control of both Type I (juvenile onset) and Type II (adult onset) diabetes. Insulin, unfortunately, constitutes an example of molecules which do not readily diffuse through the stratum corneum at a therapeutically useful rate.

While there have been attempts in the prior art to develop transdermal "patches" which contain a particular amount of insulin, which may be transferred at a particular rate, these patches have numerous limitations. One specific limitation is that insulin users must often gauge their requirements relative to physical activity and ingestion of carbohydrates. Additionally, there are different types of insulin, e.g. long-acting and short-acting, and the patient must develop skill in blending both the type and quantity of insulin in order to adequately control their blood sugar levels. The use of multiple patches having variable dosage strengths and insulin response characteristics thus becomes problematic.

Thus there remains a longfelt need for a dermal delivery system for insulin in a convenient format, e.g. a gel or cream, which can be formulated with insulin compounds having varied release characteristics, and whereby the dosage could be determined as a function of the volume applied.

DESCRIPTION OF THE PRIOR ART

U.S. Pat. No. 6,416,772 teaches a topical dermal anesthetic composition for relief of pain comprising alcohol in an amount by weight of about 57 to about 91 percent; glycerin in an amount by weight of about 1 to about 12 percent; an analgesic agent in an amount by weight of about 2 to about 28 percent, the analgesic agent comprising a derivative of salicylic acid; methylsulfonylmethane (MSM) in an amount by weight of about 0.02 to 5 percent; and Emu oil in an amount by weight of about 0.01 to 3 percent. The composition provides transdermal pain when the analgesic agent is applied directly to an area of pain.

Alcohol, preferably ethyl or isopropyl alcohol, is taught as being necessary to effectively dissolve the analgesic so that it can be absorbed through the skin. Glycerin, in turn, is required to act as a stabilizer for the acetylsalicylic acid, triethanolamine salicylate, or other analgesic agent, such that the alcohol does not significantly affect the marketable shelf life of the composition. Glycerin is also taught as being necessary to sufficiently disperse the analgesic agent such that the composition does not need to be shaken or stirred before topical use. Methylsulfonylmethane (MSM) and Emu oil are taught as being included to help facilitate the absorption of the composition into the skin and also, due to the pain relieving characteristics in and of themselves, potentiate the analgesic to increase the efficacy of the composition.

This patent fails to teach a composition which is effective in alleviating pain when applied to various trigger points, distal from the actual perceived area of discomfort. Furthermore, the '772 patent requires the use of alcohol for transdermal delivery, which causes degradation of the analgesic, and subsequently requires glycerin as a stabilizer to retard the alcohol degradation.

U.S. Pat. No. 6,346,278 teaches a lipid extract of Perna canaliculus or Mytilus edulis as an active component, in a composition suitable for transdermal administration comprising an ointment or lotion base or vehicle, which may include a skin penetration enhancing agent to assist in administration of the active component. Suitable bases or vehicles are oils such as olive or Emu oil, administered alone or with a penetrant such as cineole or limonene.

U.S. Pat. No. 6,444,234 teaches an alcohol containing pharmaceutical compositions for the transdermal administration of a medicament or other active agent by topical application of the composition to the skin of humans or other animals. Methodology for formulating such compositions which provide for very rapid uptake of the medicament and transmigration into and through the skin to either fatty tissues or the vascular system, while minimizing irritation to the skin and/or immunological response, is based on a transdermal delivery system (TDS) wherein the medicament is modified to form a true solution in a complex formed from particular solvents and solvent and solute modifiers in combination with skin stabilizers. Analgesics such as ibuprofen and the like, MSM and Emu oil are taught as useful in combination with the transdermal delivery system.

U.S. Pat. No. 6,528,040 teaches an Emu oil-based formulation for use as an analgesic, anesthetic and antipruritic. The formulation contains 0.01 to 13 wt % alkyl esters; and 20 to 70 wt % Emu oil; 10 to 33 wt % benzyl alcohol; 10 to 33 wt % benzoin; 0.2 to 2 wt % allantoin; 0.25 to 1.25 wt % methylparaben and 0.01 to 0.30 wt % propylparaben. The formulation may be formulated as a spray or transdermal formula and may be used for treatment of chronic cutaneous ulcers and burn wounds.

U.S. Pat. No. 5,885,597 teaches a topical composition for relieving pain in a person in need of such relief, consisting essentially of an effective amount of a combination of at least one corticoid analgesic, at least one arylpropionic acid type analgesic, and at least one p-aminobenzoic acid ester type local anesthetic; an amount effective in enhancing the effectiveness in relieving pain of the combination of capsaicin, and an amount effective to increase the transmission thereof through the skin of at least one phospholipid and at least one polyoxyethylenepolyoxypropylene copolymer.

U.S. Patent Application 20030031724 teaches compositions that may be cost-effectively derived or processed from the Emu, Dromiceius novaehollandiae, and used as antiinflammatory agents in patients. The application does not contemplate the use of MSM or insulin compositions in a transdermal delivery environment.

U.S. Patent Application 20010033838 teaches the use of Emu oil and its various fractions as a carrier for antifungal, antibacterial, and antiviral medications and preparations. The use of MSM in combination with Emu oil is taught, however when transdermal application is desired the Emu oil is replaced with a liposomal or oil-based transdermal component.

U.S. Pat. No. 6,024,975 is directed toward a high molecular weight drug which is transdermally administered by applying a polymer skin enhancer and a drug active to the skin of the patient. The drug may be encapsulated or the drug solution may be partly encapsulated and partly free. The skin enhancer which is required is polyvinylpyrrolidone (PVP) and it is mixed at between 7 and 35% of the drug. A gelling agent may be optionally added at up to 20% by volume. The chemical system is preferably administered via a multidose transdermal drug patch assembly which includes a drug-impervious support impressed to form a series of compartments. Each compartment is a reservoir for a unit dose of an active drug designed to be transdermally administered. The support is adhesively secured to the skin of a patient. Individual devices are provided for resealably enclosing the drug in each of the reservoirs. The individual enclosing devices are removable to release the unit dose into contact with the skin of the patient and are actuable to control the transdermal absorption of the drug actives. The patent disclosure is largely directed toward trans-dermal medication assemblies and more particularly to such assemblies consisting of multiple unit-dose reservoirs with each reservoir having individual tear and release resealable closure means for initiation and administration of the medication. However, it is suggested that the drug may also be administered in a creme. All formulations would nevertheless require polyvinylpyrrolidone.

U.S. Pat No. 6,444,240 is directed toward compositions containing insulin formulated for topical application and a method for using the compositions for the cosmetic treatment of wrinkles.

SUMMARY OF THE INVENTION

The instant invention discloses a dermal delivery system composition comprising an aqueous base vehicle including at least one fatty acid alkyl ester having thirteen to thirty six carbon atoms, polyethylene glycol-8 (PEG-8), Emu oil, and a gelling agent. For enhanced skin penetration methylsulfonylmethane (MSM) may be added to the composition. One or more active insulin ingredients are added to this aqueous base vehicle.

Examples of suitable fatty acid alkyl esters include, albeit not limited to, methyl laurate, methyl myristate, methyl palmitate, methyl stearate, methyl behenate, ethyl oleate, ethyl linoleate, butyl oleate, butyl stearate, isopropyl myristate, isopropyl palmitate, dodecyl acetate, tetradecyl octanote, cetyl palmitate, and stearyl stearate.

The aforementioned fatty acid alkyl esters facilitate compounding and can be added to the formulation from about 0.001 to about 31.0 wt % of the composition, preferably about 3 wt %.

Examples of idoneous gelling/emulsifying agents that can be used in the present invention include guar gums, xanthan gums, carrageenan, cellulose, hydroxyalkyl celluloses, sodium carboxycelluloses, SEPIGEL 305, gelatin, agar, starch, or the like. SEPIGEL 305 is a trademark and manufactured by Seppic (Fairfield, N.J.). SEPIGEL 305 is a gelling/emulsifying agent comprising about 40% polyacrylamide, about 15% $C_{13}$-$C_{14}$ Isoparaffin and about 5% laureth-7, and q.s. water.

The gelling/emulsifying agent is added to the formulation to achieve the desired viscosity and can range from about 0.001 to about 31.0 wt %, preferably about 3 wt %.

The preferred polyethylene glycol used herein is PEG-8 (tradename PROTACHEM 400, manufacture by Protameen Chemical, Inc. Totawa, N.J.) and can be added to the formulation in amounts from about 0.001 to about 31.0 wt % of the composition, preferably about 3 wt %. Emu oil is added to the formulation to facilitate the absorption of the composition into the skin. Emu oil can be added to the instant formulation in amounts from about 0.001 to about 31.0 wt %.

In a preferred embodiment, the instant invention discloses a dermal delivery system composition comprising an aqueous base vehicle including Emu oil (American), isopropyl palmitate (tradename PROTACHEM IPP, sold by Protameen Chemical, Inc. Totawa, N.J.), PEG-8, and SEPIGEL 305 (sold by Seppic). Methylsulfonylmethane (MSM) may also be included to help facilitate the absorption of the composition into the skin.

To this base vehicle, one or more active insulin ingredients are added, e.g. HUMALOG.

As opposed to the use of injected insulin, topical creams of the instant invention have the advantage of not requiring the patient or a caregiver to give an injection; nor must the patient carry and/or transport the necessary paraphernalia required for giving an injection.

The dermal delivery system, as illustrated herein, is alcohol free and therefore does not suffer from the problems of decreased shelf-life associated with alcohol containing prior art formulations. Since alcohol is not utilized, the presence of glycerin is likewise not required. Thus, a unique alcohol-free dermal delivery system is provided which provides enhanced penetration via the dermal layers thereby enabling a safer, quick-acting, and easier-to-comply alternative to capsules and tablets.

Accordingly, it is an objective of the instant invention to provide an alcohol-free, cream base rapid dermal delivery system for transdermal dosing of insulin compositions effective for the therapeutic treatment of diabetes.

It is another objective of the instant invention to provide a process for manufacture of said dermal delivery system.

Other objects and advantages of this invention will become apparent from the following description taken in conjunction with the accompanying drawings wherein are set forth, by way of illustration and example, certain embodiments of this invention.

DETAILED DESCRIPTION OF THE INVENTION

In order to reduce to practice a dermal delivery system which provides enhanced skin penetration, it is necessary to understand the parameters which affect this phenomenon.

Various Factors Affecting Skin Penetration:

1) Oil solubility (J Pharm Sci "Linear relationships between lipophilic character and biological activity of drugs." 1972 Jan;61(1):1-19) the more oil soluble [lipophilic] the substance, the greater the skin penetration;

2) Molecular weight (the smaller the molecule, the easier penetration);

3) Creams, gels and liquids penetrate better than solids;

4) Penetration enhancers improve topical absorption of lipophilic substances (Targeted drug delivery to the skin and deeper tissues: role of physiology, solute structure and disease; Clin Exp Pharmacol Physiol 1997 Nov;24(11):874-9).

EXAMPLE 1

A non-limiting illustrative example is presented herein; the following is only an example and not solely representative of the inventive concepts discussed herein.

In accordance with a preferred embodiment of the instant invention, ingredients for a vehicle base had the following components.

| Component | Amount (wt %) |
| --- | --- |
| American Emu Oil | ~3% |
| Isopropyl Palmitate | ~3% |
| PEG-8 | ~4% |
| SEPIGEL 305 | ~3%* |

-continued

| Component | Amount (wt %) |
| --- | --- |
| Methylsulfonylmethane | ~0.75% |
| Water (DI) | q.s |

(*additional in 1% increments, if needed for gelling)

Formulation Procedure:

In order to produce the transdermal insulin delivery system/composition as set forth above, the following procedure was performed:

1. Weigh out active ingredients, incorporating about 1 unit of HUMALOG insulin per 1 gram cream;
2. Measure about 3% American Emu oil into high speed mixing apparatus;
3. Add active ingredients to Emu oil. Mix until all powder is incorporated into oil. Mixture will be very dry;
4. Measure isopropyl palmitate and PEG-8, add to Emu mixture;
5. Let mix for ½ hour;
6. Add DI water, mix for 5 minutes, scraping sides of mixing container occasionally;
7. Add about 3% SEPIGEL 305, let incorporate for 5 minutes; If desired consistency has not been achieved, add SEPIGEL 305 in 1% increments until desired consistency is achieved.

In order to produce a transdermal insulin delivery system/composition the above procedure was followed and the subsequent tests were performed to establish efficacy of the transdermal delivery system.

Application of Transdermal Cream with Insulin in Measured Dose

1. Measure off about 1 gram of mixture;
2. Apply to inside of wrist and rub in until skin feels dry;
3. Take glucose levels every ten minutes and record the readings;
4. Glucose levels dropped below 50 within 30 to 40 minutes;
5. Ingested 2 glucose tablets and 2 Hershey bars to stop sugar level drop;
6. This study was repeated on 3 different occasions thereby demonstrating that the insulin transdermally entered the circulatory system in therapeutically effective quantities thereby affecting a change in sugar levels in the body.

In accordance with this invention, an insulin composition is understood to mean any type of insulin useful in the therapeutic treatment of diabetes, used singly, or in any combination, in order to provide any desired affects. Such compositions are illustrated by, albeit not limited to various species of insulin, such as a blend of short acting insulin; long acting insulin; insulins which provide a base level concentration for a prolonged period and which can be supplemented with a second formulation for providing short acting control, and various combinations thereof.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification.

One skilled in the art will readily appreciate that the present invention is well adapted to carry out the objects and obtain the ends and advantages mentioned, as well as those inherent therein. Any compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An alcohol-free composition effective for transdermal delivery of insulin comprising in combination: an effective amount of Emu Oil, an effective amount of at least one fatty acid alkyl ester, an effective amount of polyethylene glycol, a gelling agent in an amount effective for gelling, a therapeutically effective amount of insulin, and sterile water sufficient to make 100% W/W.

2. The composition for transdermal delivery of insulin as set forth in claim 1, wherein said fatty acid alkyl ester comprises at least one member selected from the group consisting of methyl laurate, methyl myristate, methyl palmitate, methyl stearate, methyl behenate, ethyl oleate, ethyl linoleate, butyl oleate, butyl stearate, isopropyl myristate, isopropyl palmitate, dodecyl acetate, tetradecyl octanote, cetyl palmitate, and stearyl stearate.

3. The composition for transdermal delivery of insulin as set forth claim 1, wherein said gelling agent comprises at least one member selected from the group consisting of guar gums, xanthan gums, carrageenan, cellulose, hydroxyalkyl celluloses, sodium carboxycelluloses, gelling agent including a combination of about 40% polyacrylamide, about 15% $C_{13}$-$C_{14}$ iso-paraffin, about 5% laureth-7 and water in an amount sufficient to make 100% W/W gelatin, agar, starch, or the like.

4. The composition for transdermal delivery of insulin as set forth in claim 1, wherein said polyethylene glycol is polyethylene glycol-8.

5. The composition for transdermal delivery of insulin as set forth in claim 1, further comprising an effective amount of methylsulfonylmethane.

6. An alcohol-free insulin composition effective for transdermal delivery formulated by a method comprising:
   providing a therapeutically effective amount of insulin;
   providing an effective amount of Emu oil in a high speed mixing apparatus;
   adding said insulin to said Emu oil and mixing until a homogeneously blended composition is formed;
   adding an effective amount of at least one fatty acid alkyl ester and an effective amount of polyethylene glycol to said homogeneous blend, and mixing for a sufficient amount of time;
   adding an effective amount of at least one gelling agent to achieve homogeneity and a gel-like consistency after blending; and adding additional gelling agent, if necessary, until desired gel consistency is achieved;
   adding sterile water sufficient to make 100% W/W and mixing to homogeneity:
   whereby said alcohol-free insulin composition effective for transdermal delivery is produced.

* * * * *